(12) United States Patent
Xu et al.

(10) Patent No.: US 11,221,672 B2
(45) Date of Patent: Jan. 11, 2022

(54) ASYMMETRIC EEG-BASED CODING AND DECODING METHOD FOR BRAIN-COMPUTER INTERFACES

(71) Applicant: TIANJIN UNIVERSITY, Tianjin (CN)

(72) Inventors: Minpeng Xu, Tianjin (CN); Dong Ming, Tianjin (CN); Xiaolin Xiao, Tianjin (CN)

(73) Assignee: TIANJIN UNIVERSITY, Tianjin (CN)

( * ) Notice: Subject to any disclaimer, the term of this patent is extended or adjusted under 35 U.S.C. 154(b) by 0 days.

(21) Appl. No.: 16/616,834

(22) PCT Filed: Dec. 30, 2018

(86) PCT No.: PCT/CN2018/125927
§ 371 (c)(1),
(2) Date: Nov. 25, 2019

(87) PCT Pub. No.: WO2019/144776
PCT Pub. Date: Aug. 1, 2019

(65) Prior Publication Data
US 2021/0173482 A1 Jun. 10, 2021

(30) Foreign Application Priority Data

Jan. 23, 2018 (CN) .......................... 201810065388.1
Jan. 23, 2018 (CN) .......................... 201810065848.0

(51) Int. Cl.
*G06F 3/01* (2006.01)
(52) U.S. Cl.
CPC .................................. *G06F 3/015* (2013.01)
(58) Field of Classification Search
CPC .............................. G06F 3/015; G06F 3/0482
(Continued)

(56) References Cited

U.S. PATENT DOCUMENTS 10,365,716 B2 * 7/2019 Aimone ................. A61B 5/378
10,390,722 B2 * 8/2019 Guger ................... A61B 5/742
(Continued)

FOREIGN PATENT DOCUMENTS

CN 1778272 A 5/2006
CN 103150017 A 6/2013
(Continued)

OTHER PUBLICATIONS

Xiaogang Chen; Yijun Wang; Masaki Nakanishi; Tzyy-Ping Jung; Xiaorong Ga, "Hybrid frequency and phase coding for a high-speed SSVEP-based BCI speller", Aug. 26-30, 2014, 2014 36th Annual International Conference of the IEEE Engineering in Medicine and Biology Society, pp. 3993-3996 (Year: 2014).*
(Continued)

*Primary Examiner* — Calvin C Ma
(74) *Attorney, Agent, or Firm* — Dragon Sun Law Firm, PC; Jinggao Li, Esq.

(57) ABSTRACT

The present invention provides an asymmetric EEG-based coding and decoding methods for BCIs, the BCI system includes an evoked stimulus module, an acquisition module and an EEG signal data set including a training set $X_k$ and a testing sample Y, and an EEG signal decoding module; the evoked stimulus module sends a hybrid coding visual stimulus to subjects to evoke a specific EEG signal as required; the acquisition module obtains data information by amplifying and filtering the EEG signal so as to constitute EEG signal module; the decoding module coverts the data information into an instruction set for outputting the coding method of the present invention uses asymmetric characteristics of brain electrophysiological activity response to stimulus, combines with coding strategies such as SDMA, CDMA, FDMA and phase division multiple access coding.

8 Claims, 2 Drawing Sheets

(58) Field of Classification Search
USPC .......................................................... 345/156
See application file for complete search history.

(56) References Cited

U.S. PATENT DOCUMENTS

| 2012/0289869 | A1* | 11/2012 | Tyler ..................... | A61B 5/369 |
| | | | | 601/2 |
| 2017/0172447 | A1* | 6/2017 | Mitra .................... | A61B 5/6814 |
| 2017/0273585 | A1* | 9/2017 | Rudzinski .............. | A61B 5/167 |
| 2020/0268296 | A1* | 8/2020 | Alcaide ................ | A61B 5/7435 |

FOREIGN PATENT DOCUMENTS

| CN | 105824418 A | 8/2016 |
| CN | 108469896 A | 8/2018 |
| CN | 108470182 A | 8/2018 |

OTHER PUBLICATIONS

International Search Report of PCT/CN2018/125927.
Written Opinion of PCT/CN2018/125927.

* cited by examiner

ASYMMETRIC EEG-BASED CODING AND DECODING METHOD FOR BRAIN-COMPUTER INTERFACES

CROSS-REFERENCE TO RELATED APPLICATIONS

This application is a national stage application of PCT Application No. PCT/CN2018/125927. This Application claims priority from PCT Application No. PCT/CN2018/125927 filed Dec. 30, 2018, CN Application No. CN 201810065848.0 filed Jan. 23, 2018, and CN 201810065388.1 filed Jan. 23, 2018, the contents of which are incorporated herein in the entirety by reference.

Some references, which may include patents, patent applications, and various publications, are cited and discussed in the description of the present disclosure. The citation and/or discussion of such references is provided merely to clarify the description of the present disclosure and is not an admission that any such reference is "prior art" to the present disclosure described herein. All references cited and discussed in this specification are incorporated herein by reference in their entireties and to the same extent as if each reference was individually incorporated by reference.

FIELD OF THE INVENTION

The present invention relates to the technical filed of brain-computer interfaces, and in particular to an asymmetric EEG-based coding and decoding method for brain-computer interfaces.

BACKGROUND OF THE INVENTION

Brain-computer interfaces (hereinafter referred to as BICs) refer to a system that directly converts central nervous system activity into artificial output, which can replace, repair, enhance, supplement or improve the normal output of the central nervous system, thereby improving the interaction between the central nervous system and the internal and external environment. By collecting and analyzing the EEG signals of the subjects under different stimuli, and using certain techniques to establish a communication between the human brain and computers or other electronic devices, BICs realize a novel information interacting and control method, and provide a channel for the handicapped, especially those with physical motor impairment but normal thinking, to communicate and control information, so that they can communicate with outsiders or manipulate devices without language or physical movements. For this purpose, BCIs are getting more and more attention.

It is common to apply the paradigm evoked by visual stimulus in BCI systems. Among them, P300-speller based on the characteristic of P300 in Event-related Potential (ERP) and SSVEP-BCI based on Steady-state Visual Evoked Potential (SSVEP) are the most widely used, and the corresponding application has been developed more stable and mature. Due to the characteristic of nonlinear and non-stationary of the EEG signals, extracting weak EEG signals from complex background EEG is one of the important technologies of BCI systems. To overcome the interference from noisy background EEG, traditional non-invasive visual BCIs preferred to use a strong visual stimulus that extended over relatively large regions of the visual field to elicit a large neuronal population response and produce distinct EEG features. For example, the stimulating squares used in the SSVEP-BCI often subtended the most part of the central 4° of visual angle, which could span the whole fovea vision; according to the calculation of the retino-cortical map, it would directly activate about 1300 $mm^2$ of the area. For a P300-speller, a flash of a target character would directly activate an area of about 160 $mm^2$. Both the SSVEP-BCI and P300-speller can greatly reduce the performance due to reduction of cortical activation area. Therefore, traditional visual BCI system has the problems of large stimulation area, high intensity and occupation of cognitive resources, which are not conducive to users for long-term multi-task operation, and limit the further development and application of BCIs. As the typical feature of asymmetric BCIs, Asymmetric Visual Evoked Potential (aVEP) belongs to very faint lateralized visual evoked potential, the amplitude thereof usually no more than 1 µV. According to the spatial contralateral superiority of the visual stimuli response, aVEP can be evoked by unilateral stimuli that appear in the visual field.

Besides, P300-speller with P300 characteristics of the ERP and SSVEP-BCI of SSVEP are widely used visual stimulus-evoked BCI systems, and the corresponding application has been developed more stable and mature. For real-time data acquisition systems, in order to eliminate interference signals, it is usually necessary to perform digital filtering the collected data. Traditional filtering methods usually filter out specific band frequencies, such as low-pass filtering, high-pass filtering, band-pass filtering, notching, etc. Due to the characteristic of nonlinear and non-stationary of the EEG signals, extracting weak EEG signals from complex background EEG and then classifying and recognizing the signals according to the characteristics are key factors in determining the performance of BCI systems. Since the EEG signals have frequency characteristics, the filtering method is also commonly used in the processing and analysis of EEG signals. Generally, the filtering frequency bands will be adjusted according to different EEG characteristics. After filtering, the traditional methods for classifying and recognizing EEG signals include Linear Discriminant Analysis (LDA), Common Spatial Pattern (CSP), Support Vector Machine (SVM), Canonical Correlation Analysis (CCA), etc. These methods are included the idea of spatial filtering, that is, selecting one or several classification planes in a high-dimensional space, and spatially filtering the signals as a spatial filter so as to reduce the high-dimensional signal to a low-dimensional signal in order to facilitate signal classification. CCA algorithm is currently widely used in the SSVEP-BCI system, and some studies have further improved the algorithm, such as applying the template matching principle in the subject's signal in the EEG signal processing steps. Such upgraded method improves recognition accuracy rate and information transmission rate of the system, which lays a powerful foundation for the further transformation of BCIs into application results.

Therefore, a heretofore unaddressed need exists in the art to address the aforementioned deficiencies and inadequacies.

SUMMARY OF THE INVENTION

In view of the above problems, an objective of the present invention is to provide an asymmetric EEG-based coding and decoding method for BCIs. The coding method of the present invention uses asymmetric characteristics of brain electrophysiological activity response to stimulus, combines with coding strategies such as spatial division multiple access (SDMA) coding, code division multiple access (CDMA) coding, frequency division multiple access (FDMA) coding and phase division multiple access coding, effectively expanding the number of system instruction sets, providing the development of BCI systems. Meanwhile, the decoding method of the present invention is a characteristic classification method combining discriminant mode spatial filtering and template matching principle. Based on the existing template matching CCA classification scheme, the present invention introduces a spatial filtering method by using DSP algorithm in the decoding method, and constructs different decoding templates according to the coding strategies of different stimulation paradigms so as to improve the signal-to-noise ratio of the EEG signal and improve the classification and recognition efficiency of the signal characteristics.

For this purpose, the technical scheme of the present invention is as follows:

An asymmetric EEG-based coding method for BCIs, including the following steps of:

Step 1: constructing an evoked stimulus module in a BCI system;

Step 2: sending, by the evoked stimulus module, a hybrid coding visual stimulus to subjects to evoke a specific EEG signal as required;

Step 3: amplifying and filtering the EEG signal by an acquisition module so as to obtain data information;

Step 4: converting, by a decoding module, the data information into an instruction set for outputting.

The hybrid coding generated by the evoked stimulus module includes at least any two combinations of SDMA coding, CDMA coding, FDMA, and phase division multiple access coding.

The hybrid coding generated by the evoked stimulus module includes SDMA coding, CDMA coding, FDMA, and phase division multiple access coding.

For this purpose, the present invention further provides the following technical scheme:

An asymmetric EEG-based decoding method for BCIs, including the following steps of:

Step 1: constructing an EEG signal data set including a training set $X_k$ and a testing sample $Y$ based on the BCI system;

Step 2: performing frequency domain filtering and down-sampling data processing to the testing sample $Y$;

Step 3: based on Fishers linear discriminant criterion, calculating the training set $X_k$ to obtain a projection matrix $W$;

Step 4: performing spatial filtering by using DSP algorithm to the training set $X_k$ and the testing sample $Y$ to obtain eigenvector $W^T\hat{X}_k$ and $W^TY$ according to the equations (5), (6);

$$S_w^{-1}S_B * W = \begin{bmatrix} \lambda_1 & & \\ & \ddots & \\ & & \lambda_{N_c} \end{bmatrix} * W \quad (5)$$

$$S_D = \Sigma_{11} + \Sigma_{22} - \Sigma_{12} - \Sigma_{21} \quad (6)$$
$$S_w = \sigma_1^2 + \sigma_2^2$$

Step 5: based on the eigenvector $W^T\hat{X}_k$ and $W^TY$, performing spatial filtering by using CCA algorithm to construct two projection matrixes $U_k$ and $V_k$ by equation (8);

$$CCA(W^T\hat{X}_k, W^TY) = \max_{U_k, V_k} \frac{\varepsilon[U_k^T W^T \hat{X}_k Y^T W V_k]}{\sqrt{\varepsilon[U_k^T W^T \hat{X}_k \hat{X}_k^T W U_k] \cdot \delta[V_k^T W^T Y Y^T W V_k]}} \quad (8)$$

Step 6: based on the eigenvector $W^T\hat{X}_k$ and $W^TY$ and the projection matrixes $U_k$ and $V_k$, performing pattern matching to obtain an eigenvector $\rho_k$ by equation (9);

$$\rho_k = \begin{bmatrix} \rho_{k1} \\ \rho_{k2} \\ \rho_{k3} \\ \rho_{k4} \\ \rho_{k5} \end{bmatrix} = \begin{bmatrix} \mathrm{corr}(W^T\hat{X}_k, W^TY) \\ -dist(W^T\hat{X}_k, W^TY) \\ CCA(W^T\hat{X}_k, W^TY) \\ \mathrm{corr}(U_k^T W^T \hat{X}_k, U_k^T W^T Y) \\ \mathrm{corr}(V_k^T W^T \hat{X}_k, V_k^T W^T Y) \end{bmatrix}, k=1,2 \quad (9)$$

Step 7: recognizing the eigenvector $\rho_k$ by different classifier modules and then outputting them.

According to the said $X_k \in R^{N_c \times N_t \times N_s}$ are the training sets of pattern k=1, 2, $Y \in R^{N_c \times N_t}$ is the testing sample, where $N_c$ is the number of channels in which EEG is collected, $N_t$ is the length of the intercepted signal, $N_s$ is the number of samples in the training set.

Compared with the prior art, the present invention has following advantages:

The coding method of the present invention is an asymmetric EEG-based coding method for BCIs, which uses the spatial asymmetry of the population response to the stimulus, thereby performing hybrid coding including SDMA coding, CDMA coding, FDMA, and phase division multiple access coding. The parameters of the coding method can be adjusted to adapt to different user requirements and different scenarios. Furthermore, the coding method of the present invention is not limited to the visually evoked system illustrated in the present invention, and also can be applied to different BCIs such as auditory evoked BCIs and somatosensory evoked BCIs. Meanwhile, the coding method can effectively expand the number of instruction sets of the BCI system, which helps to further improve the BCIs technology and promote the application of BCIs. Not only the present invention has been applied to an EEG-based BCI system, but also it has designed and implemented a BCI-speller offline and online BCI system experiments with a 32-instruction set, which is expected to obtain considerable social and economic benefits.

The decoding method of the present invention is an asymmetric EEG-based decoding method for BCIs, which is used for classification and recognition of asymmetric EEG features and can effectively improve the SNR of the recognition signal and improve the classification accuracy. The experimental results of the above-mentioned BCI system experiments with a 32-instruction set show that the average classification accuracy rate of asymmetric EEG features is 17.88% higher than that of the traditional classification method after using the decoding method of the present invention, which proves that the present invention can further improve the BCIs technology and promote the application of BCIs. Therefore, the present invention has a wide application range.

BRIEF DESCRIPTION OF THE DRAWINGS

The accompanying drawings illustrate one or more embodiments of the present invention and, together with the written description, serve to explain the principles of the invention. Wherever possible, the same reference numbers are used throughout the drawings to refer to the same or like elements of an embodiment.

DETAILED DESCRIPTION OF THE EMBODIMENTS

The invention will be described in detail below with reference to the drawings in conjunction with the embodiments. The embodiments of the present invention are intended to understand the present invention and are not intended to limit the invention.

Brain lateralization is an important field in cognitive neuroscience. Due to the lateral effects of brain structure and function, asymmetry exists in different stimuli evoked EEG features, such as visual stimuli evoked asymmetric visual evoked potential, which reflects the asymmetry of neuronal activity between the two hemispheres of the brain.

The present invention provides an asymmetric EEG-based evoking method for BCIs, and use the spatial contralateral domination to hybrid code the SDMA coding, CDMA coding, FDMA coding and phase division multiple access coding, effectively expanding the number of system instruction sets, which is expected to obtain considerable social and economic benefits. The present invention can be used in the fields of rehabilitation of disabled persons, electronic entertainment, industrial control, etc., which is expected to obtain a perfect BCI system in the future and is expected to obtain considerable social and economic benefits. The present invention is to achieved by the following steps:

An asymmetric EEG-based coding method for BCIs, including the following steps of:

Step 1: constructing an evoked stimulus module in the BCI system;

Step 2: sending, by the evoked stimulus module, a hybrid coding visual stimulus to subjects to evoke a specific EEG signal as required;

Step 3: amplifying and filtering the EEG signal by an acquisition module so as to obtain data information;

Step 4: converting, by a decoding module, the data information into an instruction set for outputting.

The hybrid coding generated by the evoked stimulus module includes at least any two combinations of SDMA coding, CDMA coding, FDMA coding, and phase division multiple access coding.

The hybrid coding generated by the evoked stimulus module includes SDMA coding, CDMA coding, FDMA coding, and phase division multiple access coding.

Figure 1:
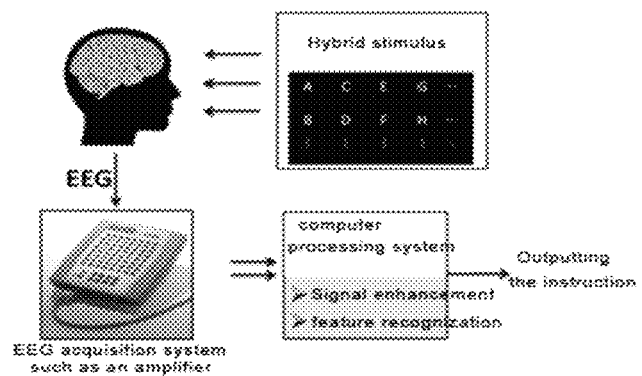
FIG. 1 is a schematic diagram of a BCI system of the present invention.
Figure 2:
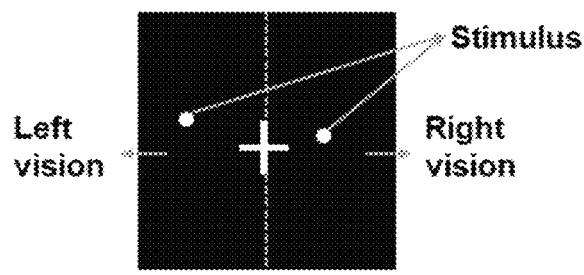
FIG. 2 is a schematic diagram of a visual division and stimuli presentation of the present invention.

The SDMA coding (as shown in FIG. 1) uses spatial information for coding, wherein up/down/left/right, which are visual divisions, corresponds to four spatial information, respectively (the left and right visions are shown in FIG. 2); and the coding information increases as the spatial information increases.

Based on SDMA scheme, the CDMA coding performs digital coding to the up/down/left/right information as code 0, 1, 2 and 3; and the coding information increases as the spatial information increases (Table 1 only shows the coding of left/right lateral spatial location).

For the FDMA coding, different stimulation cycles will evoke different frequencies, such as a successive stimulation with 100 ms will evoke a background EEG frequency of 10 Hz; for the phase division multiple access: the different stimulation starting time will change the stimulation phase.

As shown in Table 2, the hybrid coding generated by the evoked stimulus module includes SDMA coding, CDMA coding, FDMA coding, and phase division multiple access coding. The 2×2×5×2=40 hybrid coding scheme can be achieved as below: the SDMA is left/right coding; the CDMA is 0/1 two-digit CDMA coding, the FDMA includes five frequencies of 12 Hz (a 83.33 ms stimulus), 13 Hz (a 76.92 ms stimulus), 14 Hz (a 71.43 ms stimulus), 15 Hz (a 66.67 ms stimulus) and 16 Hz (a 62.5 ms stimulus); five frequencies and the phase division multiple access is 0°/90° coding.

Taking the case of evoked visual asymmetrical EEG feature as an example, FIG. 1 is a schematic diagram of a BCI system of the present invention. The BCI system includes a LCD stimulation interface, an EEG electrode, an EEG acquisition system such as an EEG amplifier and a computer processing platform. The BCI system uses the method according to the present invention for stimulation, adopts an EEG digital acquisition system of Neuroscan Ltd. to collect the EEG signals. The signals are amplified and filtered by the EEG amplifier, and then input into a computer for calculation, and finally the EEG signals are decoded and converted into the BCI instruction for outputting. Stimulus presentation and data processing analysis are run in the Matlab platform environment.

When using the system, subjects were asked to sit in front of the stimulation interface within a certain distance and focus on the center of the stimulation interface, as shown in FIG. 2, a sign of "+" is located in the center indicating the visual focus point, while the visual stimuli appeared at different positions (up/down/left/right position) will evoke different EEG signals. By using the spatial position characteristics of the EEG signal for coding, a SDMA coding scheme can be obtained. Taking a visual stimulus evoked asymmetric VEP (aVEP) as an example, visual stimuli appear in the subjects left and right vision, as shown in FIG. 2, and the aVEP EEG signal is evoked in the corresponding spatial position of the subject's brain, that is, when the stimulus appears on the left side, the right occipital area of the brain will induce more significant VEP characteristics, Meanwhile when the stimulus appears on the right side, the left occipital area of the brain will induce more significant VEP characteristics.

The parameters such as stimulus shape and area can be adjusted according to different requirements. Taking FIG. 2 as an example, a white dot with diameter of 2 mm appears in FIG. 2, the stimulus generated in the left visual side is regarded as code "0", the stimulus generated in the right visual side is regarded as code "1". By using the "0/1" binary coding strategy and adding CDMA scheme according to visual stimuli sequence at different times, the space and code hybrid coding scheme of the present invention can be achieved. Taking the 4 characters "ABCD" as an example, the hybrid coding can be achieved by encoding "left/right" by SDMA scheme and encoding code "0/1" by CDMA, as shown in Table 1.

TABLE 1

Space and code hybrid coding scheme

| Character | Spatial position of stimuli | Code sequence (two-digit) |
|---|---|---|
| A | First left stimulus, and then left stimulus | 00 |
| B | First left stimulus, and then right stimulus | 01 |
| C | First right stimulus, and then left stimulus | 10 |
| D | First right stimulus, and then right stimulus | 11 |

Different stimulation time will change the frequency evoked by the successive stimuli (e.g. FDMA coding), such as a successive stimulation with 100 ms will evoke a background EEG frequency of 10 Hz, a successive stimulation with 50 ms will evoke a background EEG frequency of 20 Hz, and different stimulation starting time will change the stimulation phase (e.g. phase division multiple access coding). Taking two frequencies (10/20 Hz) and two phase coding (0°/90°) as an example, the coding scheme of characters A to H, shown in table 2, can be achieved by encoding one-digit code "0/1" by CDMA.

TABLE 2

Hybrid coding scheme based on SDMA, CDMA, FDMA and phase division multiple access coding

| Character | Spatial position of stimulus | Code sequence (one-digit) | Frequency (Hz) | Phase (°) |
|---|---|---|---|---|
| A | Left | 0 | 10 | 0 |
| B | Left | 0 | 10 | 90 |
| C | Left | 0 | 20 | 0 |
| D | Left | 0 | 20 | 90 |
| E | right | 1 | 10 | 0 |
| F | right | 1 | 10 | 90 |
| G | right | 1 | 20 | 0 |
| H | right | 1 | 20 | 90 |

Comparing Table 1 and Table 2, it can be seen that the frequency and phase coding schemes can effectively expand the instruction set, and the number of instruction sets can be expanded by increasing the digit number of the CDMA. Furthermore, parameters such as the duration of stimulation and its duty ratio, repetition times of the stimuli sequence, interval time between two sequences can be adjusted according to actual requirements, and then the collected EEG signal is decoded so as to position the target character which is gazed by the subject. Take an example of achieving a stimulus paradigm of 40 instruction set, the hybrid coding scheme can be achieved by adopting the left/right SDMA coding; 0/1 two-digit CDMA coding, FDMA coding of five frequencies including 12 Hz (a 83.33 ms stimulus), 13 Hz (a 76.92 ms stimulus), 14 Hz (a 71.43 ms stimulus), 15 Hz (a 66.67 ms stimulus) and 16 Hz (a 62.5 ms stimulus). Table 2 shows a coding scheme, having two spatial positions, two-digit, two frequencies and two phase coding, can encode 40 characters. And if any one of the parameters is increased, such as spatial position, frequency and phase, the number of characters can be increased.

An asymmetric EEG-based decoding method for BCIs, of the present invention including the following steps of:

FIG. 1 can also represent a schematic diagram of a BCI system with a 32-instruction set of the present invention. The BCI system includes a LCD stimulation interface, an EEG electrode, an EEG acquisition system such as an EEG amplifier and a computer processing platform. The BCI system applies visual stimulus paradigm coding to evoke two patterns of asymmetric EEG features, adopts an EEG digital acquisition system of Neuroscan Ltd. to collect the EEG signals. The signals are amplified and filtered by the EEG amplifier, and then input into a computer for classifying the two EEG features, and finally the EEG signals are decoded and converted into the BCI instruction for outputting. Stimulus presentation and data processing analysis are run in the Matlab platform environment.

The SNR of two asymmetric EEG signals are −17.98 dB and −14.90 dB, wherein SNR represents ratio of signal energy to noise energy, which could be estimated as:

$$SNR = 10 \times \log_{10} \frac{\left(\frac{1}{N}\sum_{i=1}^{N} AMP_i\right)^2}{\frac{1}{N}\sum_{i=1}^{N} AMP_i^2 - \left(\frac{1}{N}\sum_{i=1}^{N} AMP_i\right)^2} \quad (11)$$

Where $AMP_i$ is the amplitude of the target potential in the $i^{th}$ trial, N is the number of trials.

Twelve subjects are tested the BCI system of the present invention, and the experiment results demonstrate that after applying the present invention, the average classification accuracy rate of the 12 subjects is increased by 17.88%, the accuracy improvement was significant (the paired T-test results are: $t_{11}=-8.91$, $p<0.01$), and the SNR of two patterns after the spatial filter by using the DSP algorithm was improved to −9.71 dB and −8.68 dB, respectively.

Figure 3:
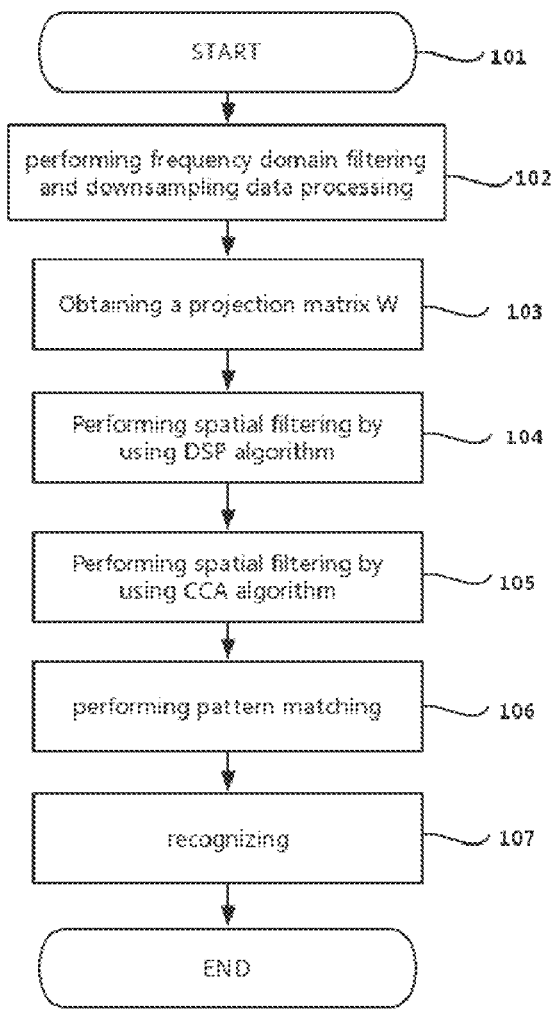
FIG. 3 is a flow chart of a method for recognizing the asymmetric EEG feature of the present invention.

As shown in FIG. 3, the present invention provides an asymmetric EEG-based decoding method for BCIs, including the following steps of:

Step 101, constructing an EEG signal data set including a training set $X_k$ and a testing sample Y based on the BCI system;

Suppose $X_k \in R^{N_c \times N_t \times N_s}$ are the training sets of pattern k=1, 2, $Y \in R^{N_c \times N_t}$ is the testing sample, where $N_c$ is the number of channels in which EEG is collected, $N_t$ is the length of the intercepted signal, $N_s$ is the number of samples in the training set. They are both zero mean across time, that is, value $s_t$ at each time point minus the time average value $\bar{s}$ in the time window $[t_1, t_2]$, which could be estimated by equation (1):

$$\hat{s}_t = s_t - \bar{s}, t \in [t_1, t_2] \quad (1)$$

The template of pattern k, written as $\hat{X}_k \in R^{N_c \times N_t}$, is the average across training samples. The covariance matrix of $$\begin{bmatrix} \hat{X}_1 \\ \hat{X}_2 \end{bmatrix}$$

is written as:

$$\Sigma = \begin{bmatrix} \Sigma_{11} & \Sigma_{12} \\ \Sigma_{21} & \Sigma_{22} \end{bmatrix} = \begin{bmatrix} \hat{X}_1 \hat{X}_1^T & \hat{X}_1 \hat{X}_2^T \\ \hat{X}_2 \hat{X}_1^T & \hat{X}_2 \hat{X}_2^T \end{bmatrix} \quad (2)$$

The variances of $X_1$ and $X_2$ are $$\sigma_1^2 = \frac{1}{N}\sum_{i=1}^{N_s}(X_{1,i}-\hat{X}_1)(X_{1,i}-\hat{X}_1)^T \quad (3)$$

$$\sigma_2^2 = \frac{1}{N}\sum_{i=1}^{N_s}(X_{2,i}-\hat{X}_2)(X_{2,i}-\hat{X}_2)^T \quad (4)$$

Step 102: performing frequency domain filtering and downsampling data processing to the testing sample $Y \in R^{N_c \times N_t}$ selected from the EEG signal date set;

Step 103: based on Fisher's linear discriminant criterion, calculating the training set $X_k$ to obtain a projection matrix $W$;

Step 104: performing spatial filtering by using DSP algorithm to the training set $X_k$ and the testing sample Y to obtain eigenvector $W^T\hat{X}_k$ and $W^T Y$ according to the equations (5), (6);

Based on Fisher's linear discriminant criterion, DSP finds a projection matrix W which could be regarded as a set of spatial filters to make the two patterns more discriminative after transformation. The matrix W can be used as a spatial filter and the solution algorithms are:

$$S_w^{-1}S_B * W = \begin{bmatrix} \lambda_1 & & \\ & \ddots & \\ & & \lambda_{N_c} \end{bmatrix} * W \quad (5)$$

$$S_D = \Sigma_{11} + \Sigma_{22} - \Sigma_{12} - \Sigma_{21} \quad (6)$$

$$S_w = \sigma_1^2 + \sigma_2^2 \quad (7)$$

Where $\lambda_i$ is the eigenvector of $i^{th}$ column of W, $N_w$ is the number of the selected spatial filters. After removing the common mode noise by W, the CCA algorithm is used to reveal the underlying correlation between $W^T\hat{X}_k$ and $W^T Y$ by finding two projection matrixes, $U_k$, $V_k$, which equals to solve CCA by equation (8).

Step 105: based on the eigenvector $W^T\hat{X}_k$ and $W^T Y$, performing spatial filtering by using CCA algorithm to construct two projection matrixes $U_k$ and $V_k$ by equation (8);

$$CCA(W^T\hat{X}_k, W^T Y) = \max_{U_k,V_k} \frac{\varepsilon[U_k^T W^T \hat{X}_k Y^T W V_k]}{\sqrt{\varepsilon[U_k^T W^T \hat{X}_k \hat{X}_k^T W U_k] \cdot \delta[V_k^T W^T Y Y^T W V_k]}} \quad (8)$$

where $\varepsilon[\cdot]$ is the mathematical expectation. Canonical correlation analysis is a statistical analysis method that measures the linear correlation between two multidimensional variables. Different from linear regression, using straight lines to fit sample points, CCA treats multidimensional feature vectors as a whole, and uses mathematical methods to find a set of optimal solutions, so that the two entities have the greatest correlation weight, that is, have the largest value calculated by formula (8). This is the purpose of a typical correlation analysis.

Step 106: based on the obtained eigenvector $W^T\hat{X}_k$ and $W^T Y$ and the projection matrixes $U_k$ and $V_k$, performing pattern matching to obtain an eigenvector $\rho_k$ by equation (9);

In pattern matching, the training template is constructed by the data of the training set, and the templates can be adjusted according to the different simulation types. Taking the classification of asymmetric EEG signals as an example, the similarity between the training template and the testing sample Y is represented as a vector $\rho_k$ shown in equation (9);

$$\rho_k = \begin{bmatrix} \rho_{k1} \\ \rho_{k2} \\ \rho_{k3} \\ \rho_{k4} \\ \rho_{k5} \end{bmatrix} = \begin{bmatrix} \text{corr}(W^T\hat{X}_k, W^T Y) \\ -\text{dist}(W^T\hat{X}_k, W^T Y) \\ CCA(W^T\hat{X}_k, W^T Y) \\ \text{corr}(U_k^T W^T\hat{X}_k, U_k^T W^T Y) \\ \text{corr}(V_k^T W^T\hat{X}_k, V_k^T W^T Y) \end{bmatrix}, k=1,2 \quad (9)$$

Where corr(*) refers to the Pearson's correlation, dict(*) refers to the Euclidean distance. More similar it is between Y and $\hat{X}_k$, more larger the $\rho_{k1}$, $\rho_{k2}$, $\rho_{k3}$, $\rho_{k4}$ and $\rho_{k5}$ will be, and $\rho_{k6}$ are connected to obtain the feature vector $\rho_k$.

Step 107: recognizing the eigenvector $\rho_k$ by different classifier modules and then outputting them.

Linear Discriminant Analysis (LDA), Common Spatial Pattern (CSP), Support Vector Machine (SVM)

According to the feature vector $\rho_k$, different classifier models of different recognition algorithms such as Linear Discriminant Analysis (LDA) and Support Vector Machine (SVM) are established. The testing sample Y is sent to the classifier for recognition after preprocessing and feature extraction, thereby predicting the type of the sample and outputting the result.

Although the functions and working processes of the present invention have been described above with reference to the accompanying drawings, the present invention is not limited thereto. The foregoing specific implementations are merely illustrative but not limiting. A person of ordinary skill in the art may make various forms under the teaching of the present invention without departing from the purpose of the present invention and the protection scope of the appended claims, and all the forms shall fall into the protection scope of the present invention.

The foregoing description of the exemplary embodiments of the present invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. An asymmetric EEG-based coding method for BCIs, comprising the following steps of:
   Step 1: performing hybrid coding comprising the SDMA coding, CDMA coding, FDMA, and phase division multiple access coding, and constructing an evoked stimulus module in a BCI system;

Step 2: sending, by the evoked stimulus module, a hybrid coding visual stimulus to subjects to evoke a specific EEG signal as required;

Step 3: amplifying and filtering the EEG signal by an acquisition module so as to obtain data information; and Step 4: converting, by a decoding module, the data information into an instruction set for outputting.

2. The coding method of claim 1, wherein the hybrid coding generated by the evoked stimulus module comprises at least any two combinations of SDMA coding, CDMA coding, FDMA, and phase division multiple access coding.

3. The coding method of claim 2, wherein the hybrid coding generated by the evoked stimulus module comprises SDMA coding, CDMA coding, FDMA, and phase division multiple access coding.

4. An asymmetric EEG-based decoding method for BCIs, comprising the following steps of:

Step 1: constructing an EEG signal data set including a training set $X_k$ and a testing sample Y based on the BCI system;

Step 2: performing frequency domain filtering and down-sampling data processing to the testing sample Y;

Step 3: based on Fisher's linear discriminant criterion, calculating the training set $X_k$ to obtain a projection matrix W;

Step 4: performing spatial filtering by using DSP algorithm to the training set $X_k$ and the testing sample Y to obtain eigenvector $W^T \hat{X}_k$ and $W^T Y$ according to the equations (5), (6);

$$S_w^{-1} S_B * W = \begin{bmatrix} \lambda_1 & & \\ & \ddots & \\ & & \lambda_{N_c} \end{bmatrix} * W \quad (5)$$

$$S_D = \Sigma_{11} + \Sigma_{22} - \Sigma_{12} - \Sigma_{21} \quad (6)$$
$$S_w = \sigma_1^2 + \sigma_2^2$$

Step 5: based on the eigenvector $W^T \hat{X}_k$ and $W^T Y$, performing spatial filtering by using CCA algorithm to construct two projection matrixes $U_k$ and $V_k$ by equation (8);

$$CCA(W^T \hat{X}_k, W^T Y) = \max_{U_k, V_k} \frac{\varepsilon[U_k^T W^T \hat{X}_k Y^T W V_k]}{\sqrt{\varepsilon[U_k^T W^T \hat{X}_k \hat{X}_k^T W U_k] \cdot \delta[V_k^T W^T Y Y^T W V_k]}} \quad (8)$$

Step 6: based on the eigenvector $W^T \hat{X}_k$, $W^T Y$ and, the projection matrixes $U_k$ and $V_k$, performing pattern matching to obtain an eigenvector $\rho_k$ by equation (9);

$$\rho_k = \begin{bmatrix} \rho_{k1} \\ \rho_{k2} \\ \rho_{k3} \\ \rho_{k4} \\ \rho_{k5} \end{bmatrix} = \begin{bmatrix} \mathrm{corr}(W^T \hat{X}_k, W^T Y) \\ -dist(W^T \hat{X}_k, W^T Y) \\ CCA(W^T \hat{X}_k, W^T Y) \\ \mathrm{corr}(U_k^T W^T \hat{X}_k, U_k^T W^T Y) \\ \mathrm{corr}(V_k^T W^T \hat{X}_k, V_k^T W^T Y) \end{bmatrix}, k = 1, 2 \quad (9)$$

and Step 7: recognizing the eigenvector $\rho_k$ by different classifier modules and then outputting them.

5. The decoding method of claim 4, wherein $X_k \in R^{N_c \times N_f \times N_s}$ are the training sets of pattern k=1, 2, $Y \in R^{N_c \times N_t}$ is the testing sample, where $N_c$ is the number of channels in which EEG is collected, $N_t$ is the length of the intercepted signal, and $N_s$ is the number of samples in the training set.

6. An asymmetric EEG-based coding method for BCIs, comprising the following steps of:

Step 1: constructing an evoked stimulus module in a BCI system;

Step 2: sending, by the evoked stimulus module, a hybrid coding visual stimulus to subjects to evoke a specific EEG signal as required;

Step 3: amplifying and filtering the EEG signal by an acquisition module so as to obtain data information; and Step 4: converting, by a decoding module, the data information into an instruction set for outputting, wherein the hybrid coding generated by the evoked stimulus module comprises SDMA coding, CDMA coding, FDMA, and phase division multiple access coding.

7. The coding method of claim 6, wherein the coding method is applied to an auditory evoked BCI.

8. The coding method of claim 6, wherein the coding method is applied to a somatosensory evoked BCI.

* * * * *